(12) United States Patent
Reynolds

(10) Patent No.: US 10,417,759 B2
(45) Date of Patent: Sep. 17, 2019

(54) MEDICAL IMAGE DATA PROCESSING SYSTEM AND METHOD

(71) Applicant: Toshiba Medical Systems Corporation, Otawara-shi (JP)

(72) Inventor: Steven Reynolds, Edinburgh (GB)

(73) Assignee: Canon Medical Systems Corporation, Otawara-shi (JP)

(*) Notice: Subject to any disclaimer, the term of this patent is extended or adjusted under 35 U.S.C. 154(b) by 190 days.

(21) Appl. No.: 15/069,564

(22) Filed: Mar. 14, 2016

(65) Prior Publication Data

US 2017/0262978 A1 Sep. 14, 2017

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/055* (2013.01); *A61B 6/032* (2013.01); *A61B 6/037* (2013.01); *A61B 8/483* (2013.01); *G06K 9/4604* (2013.01); *G06K 9/52* (2013.01); *G06T 3/0037* (2013.01); *G06T 7/10* (2017.01); *G06T 7/60* (2013.01);
(Continued)

(58) Field of Classification Search
CPC ......... G06T 5/00; G06T 5/001; G06T 7/0012; G06T 7/10; G06T 7/11; G06T 7/50; G06T 7/60; G06T 11/003; G06T 15/06; G06T 15/08; G06T 2207/30004; G06T 2207/30008; G06T 2207/30036; G06T 3/0037; G06T 19/00; G06T 2207/20024; G06T 2207/20112; G06T 2200/04; G06T 2215/06; G06T 2215/008; G06K 2009/366; G06K 9/4604; G06K 9/52; G01R 33/5608; A61B 5/055; A61B 6/032; A61B 6/037; A61B 8/483
USPC ....... 382/100, 128, 131, 132, 154, 173, 181, 382/254, 256, 260, 275, 276, 282, 299, 382/300

See application file for complete search history.

(56) References Cited

U.S. PATENT DOCUMENTS 7,693,318 B1* 4/2010 Stalling ................. G06T 11/006 382/128
7,778,392 B1* 8/2010 Berman ................. G06T 11/006 378/210

(Continued)

OTHER PUBLICATIONS

Anders Landström, et al., "Image Reconstruction by Prioritized Incremental Normalized Convolution" In Proceedings of Image Analysis—17th Scandinavian Conference, May 2011, 10 pages.

(Continued)

*Primary Examiner* — Eric Rush
(74) *Attorney, Agent, or Firm* — Oblon, McClelland, Maier & Neustadt, L.L.P.

(57) ABSTRACT

A medical image data processing system comprises processing circuitry configured to receive a three-dimensional medical imaging data set, process the three-dimensional medical imaging data set to determine a curved plane that has a shape representative of a shape of at least one anatomical structure, wherein the at least one anatomical structure comprises a plurality of sub-structures, and obtain an image based on values of the medical imaging data set at a plurality of sample points of the curved plane.

17 Claims, 6 Drawing Sheets

(51) Int. Cl.
  *G06T 15/06* (2011.01)
  *G06T 11/00* (2006.01)
  *G06T 7/10* (2017.01)
  *A61B 5/055* (2006.01)
  *A61B 6/03* (2006.01)
  *A61B 8/08* (2006.01)
  *G06K 9/46* (2006.01)
  *G06K 9/52* (2006.01)
  *G06T 7/60* (2017.01)
  *G06T 3/00* (2006.01)
  *G06T 15/08* (2011.01)
  *G06T 19/00* (2011.01)
  *G01R 33/56* (2006.01)

(52) U.S. Cl.
  CPC ............ *G06T 11/003* (2013.01); *G06T 15/06* (2013.01); *G06T 15/08* (2013.01); *G06T 19/00* (2013.01); *G01R 33/5608* (2013.01); *G06T 2200/04* (2013.01); *G06T 2207/20024* (2013.01); *G06T 2207/20112* (2013.01); *G06T 2207/30004* (2013.01); *G06T 2207/30008* (2013.01); *G06T 2215/06* (2013.01); *G06T 2219/008* (2013.01)

(56) References Cited

U.S. PATENT DOCUMENTS

| | | | | |
|---|---|---|---|---|
| 7,839,402 | B2* | 11/2010 | Dekel | G06T 15/08 382/128 |
| 9,147,280 | B2* | 9/2015 | Murphy | G06T 15/08 |
| 9,547,906 | B2* | 1/2017 | El-Zehiry | G06T 7/11 |
| 9,665,947 | B2* | 5/2017 | Kaftan | G06T 7/344 |
| 2003/0048936 | A1* | 3/2003 | Fan | G06T 7/11 382/131 |
| 2003/0086599 | A1* | 5/2003 | Armato, III | G06T 7/0012 382/131 |
| 2005/0010107 | A1* | 1/2005 | Shen | G06T 7/0012 600/425 |
| 2006/0173272 | A1* | 8/2006 | Qing | G06T 7/12 600/407 |
| 2006/0228015 | A1* | 10/2006 | Brockway | G06T 7/0012 382/132 |
| 2008/0044074 | A1* | 2/2008 | Jerebko | G06T 7/12 382/128 |
| 2008/0107318 | A1* | 5/2008 | Kiraly | G06T 17/00 382/131 |
| 2008/0317322 | A1* | 12/2008 | Acharyya | G06T 7/0012 382/132 |
| 2009/0318800 | A1* | 12/2009 | Gundel | G06T 15/08 382/131 |
| 2013/0070996 | A1* | 3/2013 | Liu | G06K 9/00 382/131 |
| 2013/0077841 | A1 | 3/2013 | Wu et al. | |
| 2013/0101197 | A1* | 4/2013 | Kaftan | G06T 5/00 382/131 |
| 2013/0150704 | A1* | 6/2013 | Vitek | A61B 5/055 600/411 |
| 2013/0249913 | A1* | 9/2013 | Smout | G06T 15/08 345/424 |
| 2015/0131881 | A1* | 5/2015 | Gnanamani | G06T 7/0012 382/131 |
| 2015/0363963 | A1* | 12/2015 | Zhan | G06T 7/11 600/410 |
| 2017/0256090 | A1* | 9/2017 | Zhou | G06T 15/08 |

OTHER PUBLICATIONS

Hans Knutsson, et al., "Normalized and Differential Convolution: Methods for Interpolation and Filtering of Incomplete and Uncertain Data" In Proceedings of IEEE Computer Society Conference on Computer Vision and Pattern Recognition, Jun. 1993, 10 pages.

"Rib fractures easier to identify with "unfolding" rib CT software" Applied Radiology, http://www.appliedradiology.com/articles/rib-fractures-easier-to-identify-with-unfolding-rib-ct-software, Jul. 2015, 3 pages.

"Highlights from the MDCT 2014 Workstation Face-off" Carestream Health Blog, http://www.carestream.com/blog/2014/06/17/highlights-from-the-mdct-2014-workstation-face-off/, 2014, 6 pages.

"Map Projection" Wikipedia, https://en.wikipedia.org/wiki/Map_projection, 2016, 11 pages.

* cited by examiner

MEDICAL IMAGE DATA PROCESSING SYSTEM AND METHOD

FIELD

The present invention relates to a medical image data processing system and method, for example a system and method that may be used to visualise anatomical structures.

BACKGROUND

There is a need for clinicians to be able to identify and count displaced and non-displaced fractures or bone lesions when performing chest examinations. For example, it is necessary to ensure that all ribs have been examined and to determine in which rib any fractures or lesions are located.

A variety of medical imaging modalities, for example computerized tomography (CT), magnetic resonance imaging (MRI) and positron emission tomography (PET), have become standard techniques for obtaining three-dimensional medical imaging data representative of a patient or other subject for diagnostic or other purposes.

It is known to use axial and oblique multi-planar reformatting (MPR) views generated from CT data or other medical imaging modalities in order to view ribs of a patient or other subject and to identify any fractures. An axial or oblique MPR view may comprise an axial or oblique slice through a set of three-dimensional image data, for example a slice across the torso of a patient. A clinician may view the ribs of the patient by stepping through a series of axial or oblique slices in turn. Each slice may include at least part of one or more ribs. Different ribs may be shown on different slices. An individual rib may appear on multiple slices.

In practice, using such techniques it can be difficult for a clinician to ensure that all ribs have been properly examined. Furthermore, once a fracture has been identified it can be difficult to identify the particular rib in which the fracture is present. Since each slice only shows a particular rib or ribs, it can be difficult to tell which rib is shown on a given slice. It may also be time-consuming for the clinician to step through the set of axial or oblique MPR views.

It has been suggested to use a rib centreline tracking algorithm to define a curved planar reformatting (CPR) image for each rib. A composite image is then generated from the collection of CPR images of the ribs and a CPR image of the spine. Effectively, each rib is shown in straightened form in the image. In principle such techniques can make non-displaced fractures more easily visible. However, the straightening of the ribs in the image can make the relative position and orientation of the ribs difficult to understand. The straightening of the ribs may make the image look unnatural. Furthermore, in some methods in which a composite image has been generated, there may appear to be discontinuities between the spine and the ribs in the generated composite image.

It has also been suggested to generate an unfolded maximum intensity projection (MIP) image of the ribcage in order to identify fractures. Such an unfolded MIP image can, in principle, give an excellent overall view of the ribcage. However, views generated using intensity projection techniques, such as MIP, can effectively hide non-displaced fractures, particularly if they are partial fractures.

MIP selects points of maximum intensity, for example by returning the highest intensity along a ray. For a fractured bone, particularly one with a partial fracture, maximum values of intensity may occur at points that are not on the fracture. Therefore in some circumstances MIP may not image points along the line of a fracture, making the fracture difficult or impossible to see in the resulting image.

Non-displaced fractures can be particularly challenging to identify as they can be invisible to imaging techniques that generate images representing or dominated by image data values obtained from the surface of the ribs, for example MIP and other intensity projection techniques.

DESCRIPTION

Embodiments are now described by way of non-limiting example with reference to the accompanying drawings in which.

Certain embodiments provide a medical image data processing system comprising processing circuitry configured to: receive a three-dimensional medical imaging data set; process the three-dimensional medical imaging data set to determine a curved plane that has a shape representative of a shape of at least one anatomical structure, wherein the at least one anatomical structure comprises a plurality of sub-structures; and perform a sampling process to obtain an image based on values of the medical imaging data set at a plurality of sample points of the curved plane.

Certain embodiments provide a medical image data processing method comprising: receiving a three-dimensional medical imaging data set; processing the three-dimensional medical imaging data set to determine a curved plane that has a shape representative of a shape of at least one anatomical structure, wherein the at least one anatomical structure comprises a plurality of sub-structures; and obtaining an image based on values of the medical imaging data set at a plurality of sample points of the curved plane.

Certain embodiments provide a medical imaging apparatus comprising a scanner configured to perform a scan to obtain a three-dimensional medical imaging data set, processing circuitry configured to receive a three-dimensional medical imaging data set, process the three-dimensional medical imaging data set to determine curved plane that has a shape representative of a shape of at least one anatomical structure, wherein the at least one anatomical structure comprises a plurality of sub-structures, and obtain an image based on values of the medical imaging data set at a plurality of sample points of the curved plane, and a display device configured to display the image.

Figure 1:
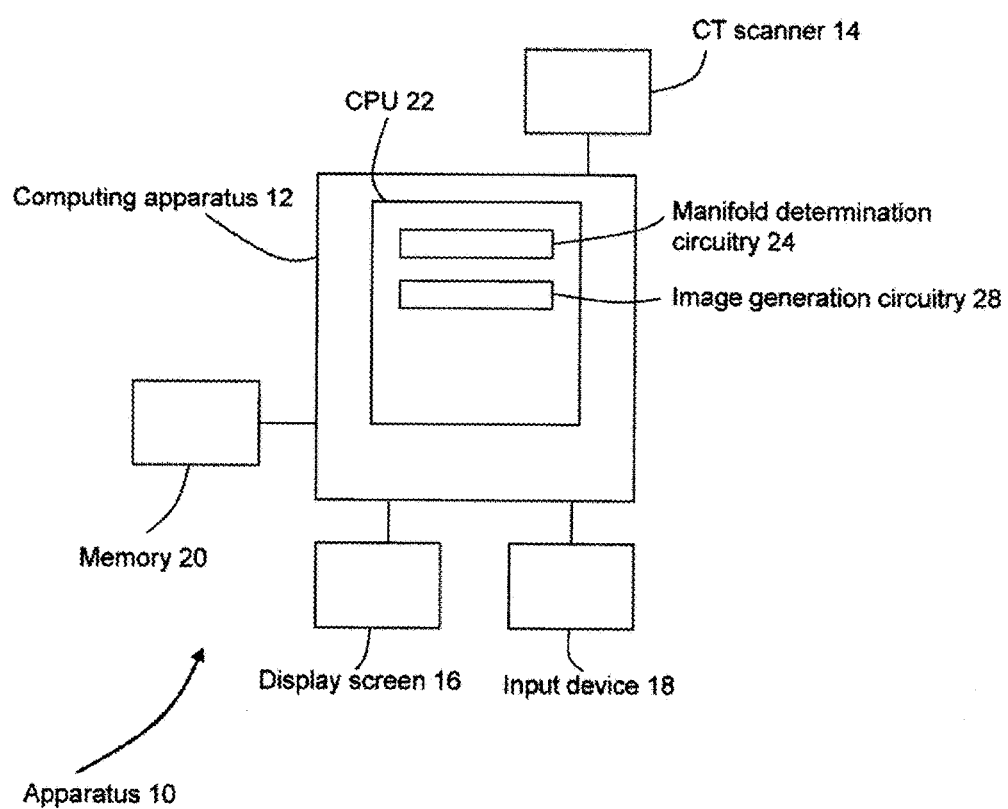
FIG. 1 is a schematic diagram of a medical imaging data processing system according to an embodiment.

A medical image data processing apparatus 10 according to an embodiment is shown in FIG. 1. The data processing apparatus 10 comprises a computing apparatus 12, in this case a personal computer (PC) or workstation, which is connected to a CT scanner 14, one or more display screens 16 or other display device, and an input device or devices 18, such as a computer keyboard, mouse or trackball.

The CT scanner 14 may be any CT scanner that is configured to obtain volumetric CT data of a region of a patient or other subject. The region of the patient or other subject may comprise at least one anatomical structure of interest. In the present embodiment, the region of the patient is the torso and the anatomical structures of interest are the ribs. In other embodiments, the anatomical structures may be any appropriate structures, for example bones such as the skull or pelvis, or organs such as the liver, heart or stomach. The volumetric CT data of the region of the patient may be reconstructed into one or more volumetric imaging data sets suitable for image processing.

In alternative embodiments, the CT scanner 14 may be replaced or supplemented by any volumetric scanner in any imaging modality that is configured to provide three-dimensional medical imaging data, for example an MRI (magnetic resonance imaging) scanner, X-ray scanner, PET (positron emission tomography) scanner, SPECT (single photon emission computed tomography) scanner, or ultrasound scanner.

In the present embodiment, volumetric CT data sets obtained by the CT scanner 14 are stored in memory 20 and subsequently provided to computing apparatus 12. In an alternative embodiment, volumetric CT data sets are supplied from a remote data store (not shown) which may form part of a Picture Archiving and Communication System (PACS). The memory 20 or remote data store may comprise any suitable form of memory storage.

Computing apparatus 12 provides a processing resource for automatically or semi-automatically processing imaging data sets, and comprises a central processing unit (CPU) 22. In the present embodiment, the computing apparatus 12 includes manifold determination circuitry 24 and image generation circuitry 28.

In the present embodiment, the manifold determination circuitry 24 and image generation circuitry 28 are each implemented in computing apparatus 12 by means of a computer program having computer-readable instructions that are executable to perform the method of the embodiment. For example, the manifold determination circuitry 24 and image generation circuitry 28 may each be implemented as a respective computer program or algorithm that is executable by the computing apparatus 12, for example by the CPU 22. However, in other embodiments, the circuitries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
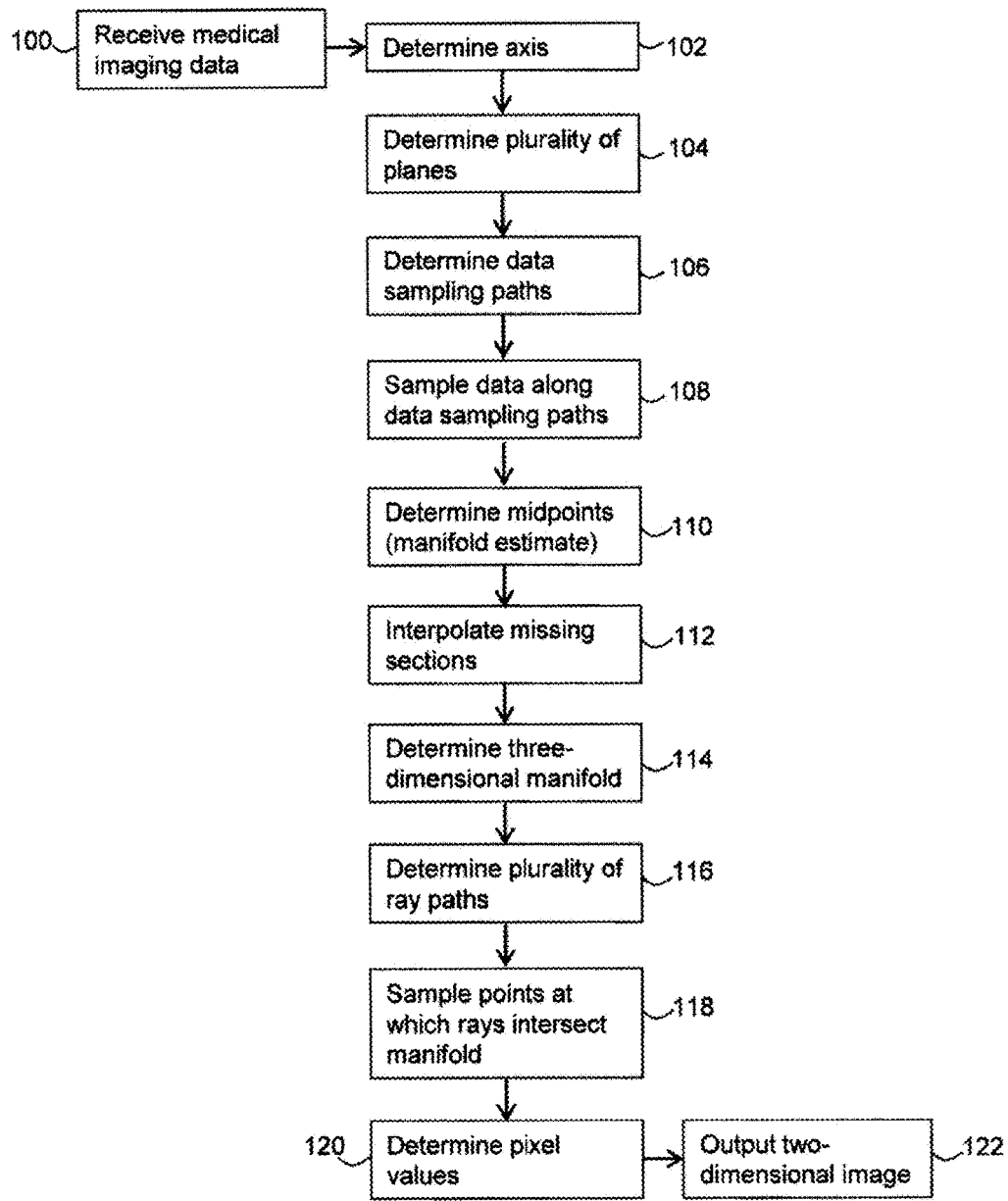
FIG. 2 is a flow chart illustrating in overview a mode of operation of the system of FIG. 1.

Operation of the system of FIG. 1 is illustrated in overview in the flow chart of FIG. 2. At a first stage 100 of the process, the computing apparatus 12 receives a medical imaging data set. In this embodiment, the medical imaging data set comprises three-dimensional CT data comprising a set of voxels, with an intensity value of each voxel representing a level of X-ray absorption determined by a CT scan at a corresponding position within a scan volume.

In alternative embodiments any other suitable modality may be used to obtain the medical imaging data set, for example magnetic resonance (MR) imaging or positron emission tomography (PET) imaging.

At the next stage 102 of the process, the manifold determination circuitry 24 determines an axis for use in a manifold determination process. The axis 200 is shown schematically in FIG. 3 and FIG. 4. In the present embodiment the axis 200 follows the superior-inferior axis of a patient that is the subject of the medical imaging data set, and is substantially aligned with the spine. In this case, the axis 200 is set from a co-ordinate system of the medical imaging data set based on the understanding that a longitudinal axis of the CT scanner and the superior-inferior axis of the patient are substantially aligned.

In other embodiments any suitable process may be used to determine the axis. For example a segmentation process may be performed on the medical imaging data set to determine the position and orientation of the spine or other anatomical structure, and the position and orientation of the axis 200 may be determined based on the segmentation.

At the next stage 104 of the process, the manifold determination circuitry 24 determines a plurality of planes 210 extending around the axis 200. It is a feature of the present embodiment that the planes 210 are tilted with respect to the axis 200 rather than extending in a direction perpendicular to the axis 200. In general each individual rib of a human patient is aligned with a plane that is tilted with respect to the direction of the spine, and by tilting the planes 210, the planes 210 may be better aligned with the ribs. In other embodiments, the planes 210 may be tilted to be substantially aligned with any appropriate anatomical structure.

Figure 4:
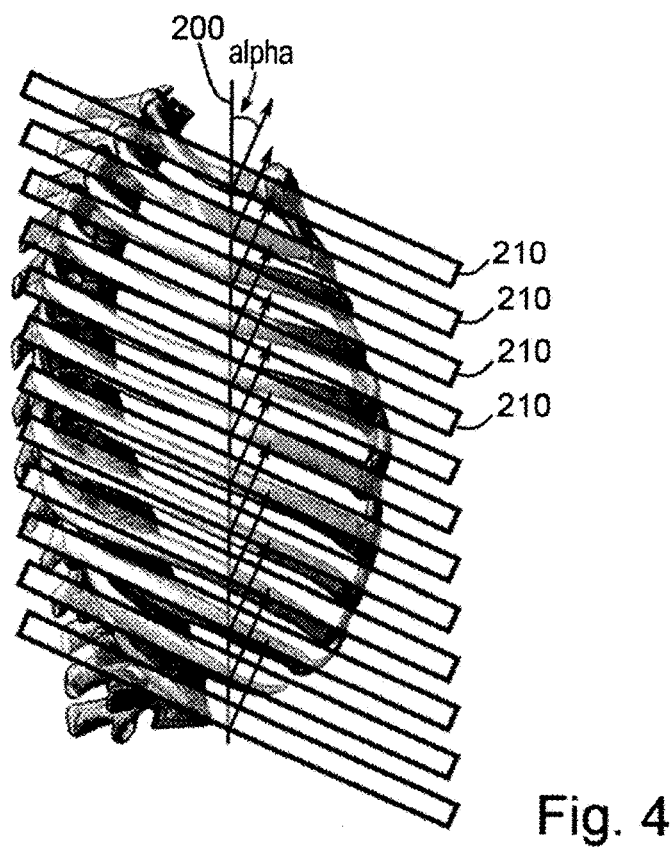
FIG. 4 is a schematic illustration of part of a plurality of the planes, showing the planes tilted with respect to a direction perpendicular to the axis.

In this embodiment, all the planes 210 have the same angle of tilt, shown as angle alpha on FIG. 4. In other embodiments, different planes 210 may have different angles of tilt. In embodiments the angle of tilt of the planes 210 may be a fixed, predetermined angle of tilt, or the angle of tilt may be determined automatically or semi-automatically, for example based on a segmentation of the medical imaging data set, and/or the angle of tilt may be determined in dependence on user input.

Figure 3:
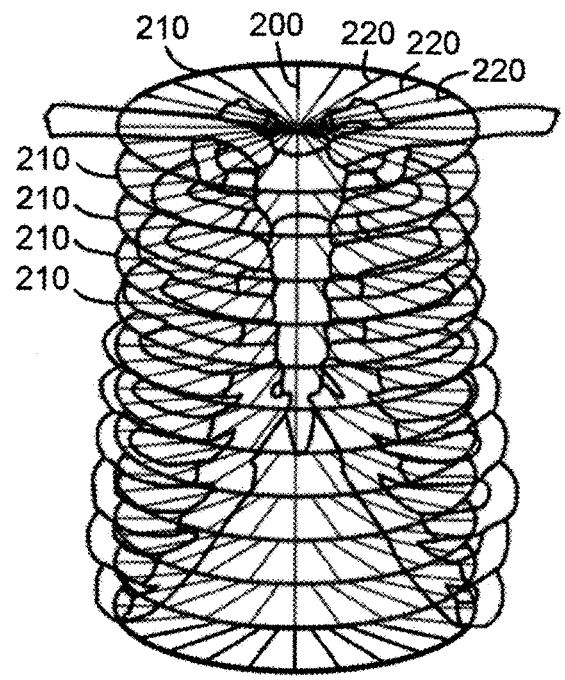
FIG. 3 is a schematic illustration of a ribcage of a subject overlaid with an axis, a plurality of planes around the axis and lines illustrating data sampling paths.

At stage 106 of the process, the manifold determination circuitry 24 determines a plurality of data sampling paths 220 on each of the planes 210. Some examples of data sampling paths 220 are shown in FIG. 3. The data sampling paths 220 extend radially with respect to the axis 200.

In the present embodiment, the plurality of data sampling paths 220 for each plane 210 are distributed over a range substantially equal to 360 degrees around the axis 200. In other embodiments, the data sampling paths 220 may be distributed over a smaller angular range. The data sampling paths 220 may be spaced at substantially equal angular intervals around the plane.

Figure 5A:
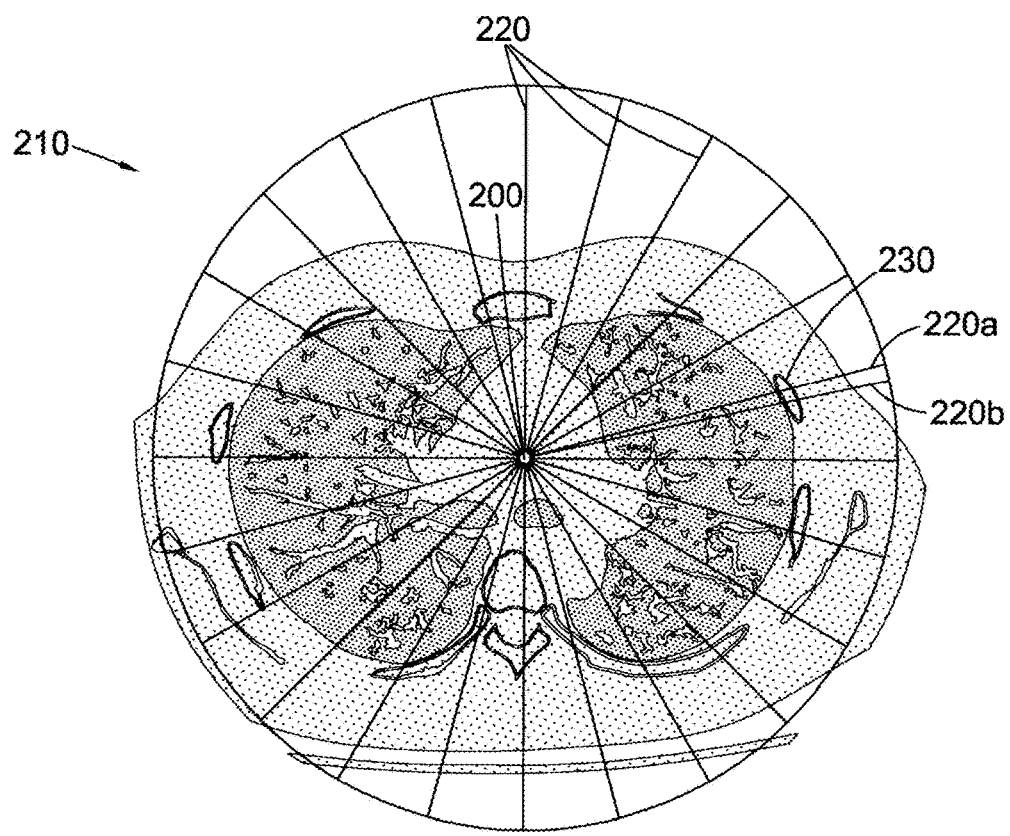
FIG. 5a is a schematic illustration showing data sampling paths extending radially from an axis and intersecting an anatomical structure represented in an imaging data set.

FIG. 5a is a schematic illustration of a single plane 210, with axis 200 at the centre of the plane 210. FIG. 5a is overlaid with a representation of a slice through the medical image data set that corresponds to the plane 210. FIG. 5a shows a plurality of data sampling paths 220 extending radially from the axis 200. For clarity, only a subset of the data sampling paths 220 that are determined in stage 106 of the process are illustrated in FIG. 5a. Further data sampling paths 220 on plane 210 exist but are not shown in FIG. 5a.

Figure 5B:
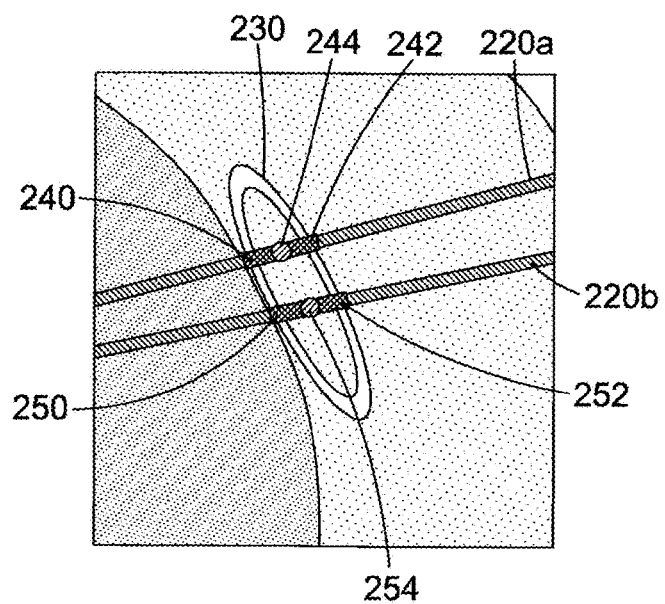
FIG. 5b is an enlarged view of a portion of FIG. 5a showing the data sampling paths passing through the anatomical structure, and including indicators of the extent of the intersection of the data sampling paths with the anatomical structure.

FIG. 5b is an enlarged view of a portion of FIG. 5a, showing a part of two data sampling paths 220a and 220b.

Each of the data sampling paths 220a and 220b intersects a region of bone 230 in the medical image data set (in this case, the bone is part of a rib). The region of bone 230 has a ring-like appearance in FIGS. 5a and 5b because the edges of the bone have a higher intensity than the middle of the bone.

At stage 108, the manifold determination circuitry 24 samples the medical imaging data set at each of a plurality of points along each data sampling path 220 by casting rays along each of the data sampling paths 220 from the axis 220. The manifold determination circuitry 24 determines an intensity value for each of the plurality of points along each data sampling path 220 from the intensity values of the medical imaging data set. In determining the intensity values for the plurality of points, the manifold determination circuitry 24 may determine a variation of intensity values of the medical imaging data along each of the plurality of data sampling paths 220.

At stages 110 to 114, the manifold determination circuitry 24 determines a curved plane that has a shape representative of a shape of at least one anatomical structure that comprises a plurality of separated sub-structures, in this case the ribcage comprising the plurality of ribs. In the described embodiment the curved plane is referred to as a manifold 400, for example a curved or complex 3D manifold, and the manifold 400 intersects all the anatomical structures of interest, which in this case are the ribs.

Any other suitable curved plane representative of a shape of the anatomical structure or structures in question, for example any suitable manifolds, may be determined according to alternative embodiments, and the curved plane may be any suitable curved two- or three-dimensional shape. The curved plane may have a minimum, negligible or zero thickness and such a curved plane may be considered to be a curved two-dimensional shape. Alternatively, the curved plane may have a non-zero or non-negligible or greater-than-minimum thickness, and thus may be a three-dimensional shape such as a slab, for example a curved slab. Such a slab may, for example, have a thickness of greater than one voxel. In contrast a line, of zero thickness and zero width, may be considered to be a one-dimensional shape even in the case where the line follows a curved path through three-dimensional space.

In the embodiment of FIG. 1, manifold determination circuitry 24 is used to determine the curved plane, in this case manifold 400. In alternative embodiments, any other suitable circuitry may be used to determine the curved plane.

At stage 110, for each data sampling path 220 that intersects at least one rib, the manifold determination circuitry 220 determines the first point (i.e. the point nearest the axis) at which the a ray cast along the data sampling path 220 intersects rib, and the last point (i.e. the point furthest from the axis) at which a ray cast along the data sampling path 220 intersects rib. The manifold determination circuitry 220 determines an estimated manifold position for the data sampling path 220, where the estimated manifold position is the midpoint between the first point and last point. The midpoint is midway between the start and end of the intersection of the ray and the rib. In other embodiments, a different method may be used to determine an estimated manifold position. For example, in some embodiments there may not be an end point to the intersection between the ray and the rib. In some embodiments, an estimated manifold position may be determined relative to the first intersection point between the ray and the rib.

FIG. 5b shows a determined first point 240, last point 242, and midpoint 244 for data sampling path 220a, and a determined first point 250, last point 252, and midpoint 254 for data sampling path 220b.

The midpoint may be within the marrow of the bone. It may be useful to use the first point and last point to find the midpoint, because in some circumstances each of the first point and last point may be better defined than the midpoint. Each of the first point and last point may have more contrast than the midpoint, since the outer parts of the bone may have greater intensity than the marrow.

In the present embodiment, the determining of the manifold by using first and last points to determine midpoints is based on an expected profile of values of intensity across the thickness of the rib, with the outer part of the rib having greater intensity than the inner part of the rib. In other embodiments, the determining of the manifold may be based on an expected profile of values of any suitable parameter across any anatomical structure of interest.

In the present embodiment, the manifold determination circuitry 24 determines the first and last point for each data sampling path 220 by using an intensity threshold to identify points having an intensity that is representative of bone, and finding the first and last points that have an intensity that is representative of bone. In other embodiments, the ribs are segmented from the medical imaging data set before stage 108 and the identification of the midpoint is performed using the segmented ribs. The first and last points are the first and last points that are labelled as rib by the segmentation. In further embodiments, any suitable method of identifying points that are part of anatomical structures of interest may be used.

In some embodiments, the first points and last points are filtered before calculating the midpoints. The intersections are stored as distances along the ray. The filtering may affect the stored distances by convolving them with their neighbours. A mid-point of the filtered distances may be used to define the manifold. Filtering the first points and last points may help to ensure that the estimated manifold position chosen for a ray forms a continuous curved plane with its neighbours.

An estimated manifold position for each data sampling path 220 that intersects a rib has been determined at stage 110. However, in the present embodiment, some data sampling paths 220 do not intersect a rib. For example, some data sampling paths 220 may pass through gaps between ribs.

At stage 112, the manifold determination circuitry 24 determines an estimated manifold position for each of the data sampling paths 220 that does not intersect a rib, by interpolating or extrapolating from the estimated manifold positions that were determined as midpoints at stage 110. For data sampling paths 220 that do not intersect any bone, the manifold determination circuitry 24 interpolates a position on a curved surface between adjacent rays that do hit the bone.

The manifold determination circuitry 24 may perform the interpolation by fitting a curve to midpoints that were determined at stage 110. The manifold determination circuitry 24 may find a plausible CPR (curved planar reformatting) surface (i.e. a plausible estimate of at least part of manifold 400) for inter rib areas by processing adjacent rays. The method of determining the estimated manifold positions for the data sampling paths 220 that do not intersect with ribs may comprise using Normalized Convolution for 2D signal reconstruction (see, for example, Anders Landström et al., Image Reconstruction by Prioritized Incremental Normalized Convolution, Image Analysis: 17$^{th}$ Scandinavian Conference, SCIA 2011, Ystad, Sweden, May 2011, Proceedings, pp 176-185 and H. Knutsson and C.-F. Westin. Normalized and differential convolution. In Proceedings of IEEE Computer Society Conference on Computer Vision and Pattern Recognition, CVPR '93, pages 515-523, June 1993).

At stage 114, the manifold determination circuitry 24 determines the manifold 400 based on the estimated manifold positions from stages 110 and 112. In some embodiments, the manifold 400 includes all of the estimated manifold positions that were determined at stages 110 and 112. In some embodiments, the manifold determination circuitry 24 adjusts at least some of the estimated manifold positions, and the manifold includes the adjusted positions. For example, the manifold determination circuitry 24 may test the estimated manifold positions for consistency with neighbouring estimated manifold positions, and adjust at least some of the estimated manifold positions if they are found to be inconsistent. In some embodiments, the manifold determination circuitry 24 builds a list of candidate rib regions for each data sampling path 220 and compares candidate regions from adjacent rays to eliminate false positives.

In some embodiments, the determined manifold 400 is a full manifold, which may comprise a continuous surface. In other embodiments, the manifold 400 is a partial manifold, which may comprise at least one discontinuous surface. For example, the manifold 400 may be defined on the ribs and may be not defined for regions between ribs. In the present embodiment, the manifold 400 is a surface that intersects all of the ribs and represents a shape of at least part of the ribcage. In other embodiments, the three-dimensional manifold 400 may intersect any appropriate anatomical structure.

The manifold determination circuitry 24 is configured to search the volume for points that match the criteria required of the manifold. In the process described above with reference to stages 100 to 114 of FIG. 2, the manifold determination circuitry 24 starts searching using a cylindrical projection, and determines points that are mid-way between the start and end of the intersection of rays defined by that cylindrical projection and ribs. In other embodiments, any suitable method of defining points on the manifold may be used. For example, a different projection system may be used. In the present embodiment, the manifold 400 is automatically derived. In other embodiments, the manifold 400 may be determined using user input.

The manifold determination circuitry 24 passes the manifold 400 to the image generation circuitry 28.

In stages 116 to 122, the manifold 400 is used to obtain a curved MPR image of the ribs using the intensity values of points on the manifold 400. The image is a two-dimensional image which presents an unfolded view of the ribs. A projection system (which in this case comprises a tilted cylindrical projection) is used to map points on the curved MPR image to be generated to points on the surface of the manifold 400.

At stage 116, the image generation circuitry 28 defines a plurality of ray paths 500 using the projection system. The number of ray paths 500 corresponds to the number of pixels to be generated.

As a first step in defining the ray paths 500, a camera axis is defined along the patient's superior-inferior axis. In the present embodiment, the defined camera axis is the same as axis 200 as shown in FIGS. 3 and 4. In other embodiments, the camera axis may be different from the axis 200 that is used in the determination of the manifold 400.

A collection of points $O^{1 \cdots N}$ are defined along the camera axis. Each point $O^i$ will correspond to a horizontal row of pixels in the output image. For each point $O^i$, a perpendicular plane $P^i$ is defined and plane $P^i$ is tilted based on an angle. In the present embodiment, the planes $P^{1 \cdots N}$ are the same as planes 210 shown in FIGS. 3 and 4 and the angle is angle alpha as shown in FIG. 4. Using tilted planes may make the ribs look more horizontal in a resulting image than if the planes were not tilted.

A collection of ray paths 500 is defined in plane $P^i$ with original $A^i$ rotating in the plane around $O^i$. In the present embodiment, the ray paths 500 are distributed around a range substantially equal to 360 degrees around the camera axis. Each ray path 500 corresponds to a different horizontal pixel in the output image for that row.

In the present embodiment, the ray paths 500 are the same as the data sampling paths 220. In other embodiments, the ray paths 500 are different from the data sampling paths 220. For example, a different projection may be used to obtain the image than was used to obtain the manifold 400. There may be more or fewer rays 500 than data sampling paths 220. For example, the number of data sampling paths 220 used to determine the manifold 220 may be greater than the number of pixels in the image, and therefore greater than the number of rays 500 used by the image generation circuitry 28.

In some embodiments, the data sampling paths 220 determined at stage 106 are used as ray paths 500 and stage 116 is omitted.

At stage 118, the image generation circuitry 28 casts rays along each of the ray paths 500. How each ray is processed will affect the output image.

In the present embodiment, the image generation circuitry 28 determines for each ray path 500 a point at which the ray cast along that ray path 500 intersects the manifold 400. Since in the present embodiment the manifold 400 has no thickness in a direction along the ray path 500, the intersection of each ray with the manifold 400 is a single point 510 on the manifold 400. The image generation circuitry 28 therefore determines a set of points 510 of corresponding number to the number of ray paths 500 (and therefore also of corresponding number to the number of pixels of the image).

In the present embodiment, the points 510 are points at which the rays cast along the ray paths 500 intersect the manifold 400. In other embodiments, the points 510 on the manifold 400 may be determined using any suitable method, which may or may not involve ray casting. Any suitable projection method may be used. The question of the unfolding of the complex manifold into the 2D imaging plane may be considered in some senses to have similar issues to those encountered in obtaining cartographic projections, for which many different approaches are known. Suitable projection methods used for cartographic projections may also be used for the present application, if so desired.

While in the present embodiment, the rays 500 are substantially contiguous with the data sampling paths 220, in other embodiments the rays 500 and data sampling paths 220 are different.

The image generation circuitry 28 samples the medical imaging data set at each of the points 510. In the present embodiment, the image generation circuitry 28 determines a voxel intensity value for each point 510 from the medical imaging data set. In other embodiments, the value of any appropriate parameter may be determined by sampling at the points 510.

Figure 6:
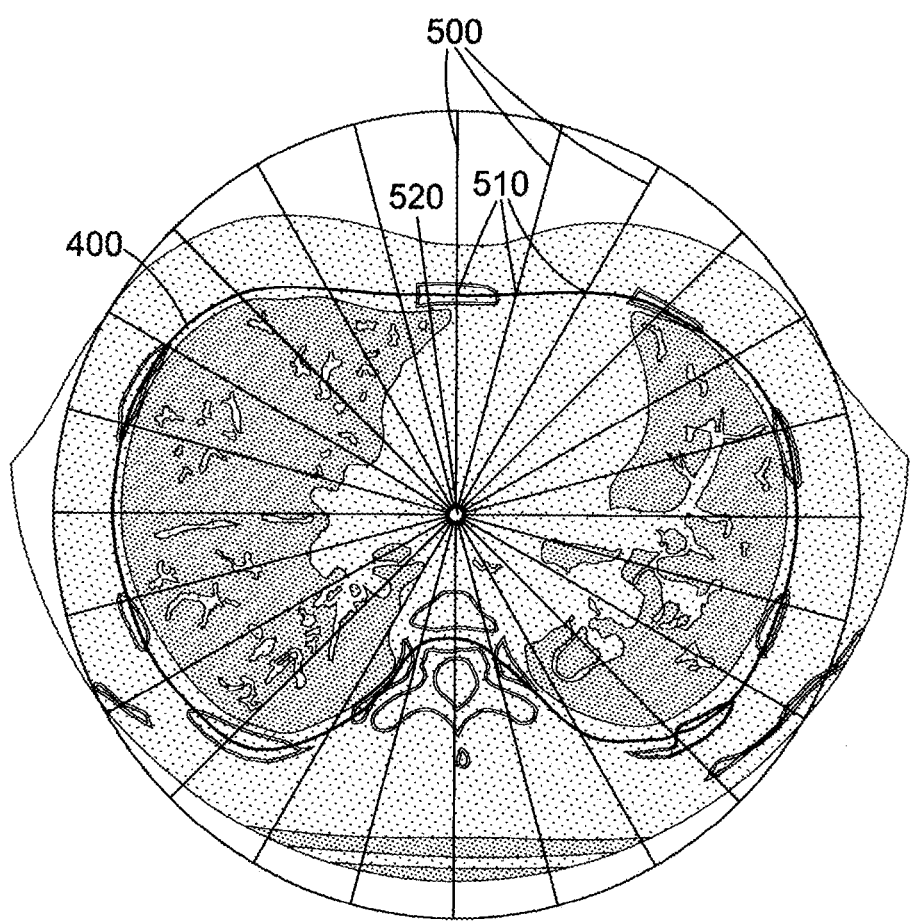
FIG. 6 is a schematic illustration of a slice through a manifold, an axis, and rays following ray paths from the axis and intersecting the manifold, overlaid with a representation of a slice through the image data from which the manifold was generated.

FIG. 6 is a schematic illustration of a slice through a manifold 400. FIG. 6 shows an axis 520, and ray paths 500.

Rays follow rays paths 500 from the axis 520 and intersect the manifold 400. The illustration of FIG. 6 is overlaid with a representation of a slice through the image data from which the manifold 400 was generated.

The rays provide a cylindrical projection that allows an unfolded view of the ribs to be obtained. The rays are used to map points in the image to points on the manifold surface. Each ray corresponds to a respective pixel of the output image.

At stage 120 the image generation circuitry 28 determines a respective pixel value for each of the plurality of ray paths 500 using the voxel intensity values sampled at stage 118. In the present embodiment, the image generation circuitry 28 determines a pixel value for each ray 500 by applying a transfer function to the voxel intensity value for the point 510 at which the ray cast along that ray path 500 intersects the manifold. The voxel intensity value for each point 510 has been determined at stage 118 by sampling the medical imaging data set.

In other embodiments, any method of obtaining a pixel value for each ray 500 may be used, and the curved plane may be in the form of a slab. The slab is obtained by giving the manifold 400 a thickness in the direction along the rays (in this case, the radial direction). In some embodiments the thickness of the slab is automatically determined. In some embodiments, the thickness may be selected by a user.

In some embodiments, slab samples are used to output a derived orthogonal/Cartesian volume in which the new volume XY corresponds to the projected image space and the X is the set of samples used in the slab offset in the ray direction. This derived volume can then be used with any other existing volumetric imaging technique, for example Shaded Volume Rendering, IP volume rendering, global illumination rendering, MPR etc.

The image generation circuitry 28 samples a number of voxels or other points along each ray (for example, 3, 4 or 5 voxels) that are nearest the intersection of the ray with the original manifold 400. The image generation circuitry 28 uses a projection of the slab to obtain the pixel value for each ray.

In some embodiments, the image generation circuitry 28 uses a maximum intensity projection of the slab to determine the pixel value for each ray. For example, the pixel value of each ray 500 may be based on the maximum value of the 3, 4, or 5 voxel values that are sampled by the image generation circuitry 28 for the ray 500. The image generation circuitry may perform an IP accumulation along the part of each ray that intersects the slab to determine the final pixel colour. In some embodiments, the image generation circuitry 28 uses a variance projection, in which pixel values are dependent on a rate of change of signal across the portion of the ray that is within the slab. In general, a collection of sample points, each offset in the ray direction, may be used to generate a slabbed image and an IP projection method may be used to determine the output result. Any suitable projection across the thickness of the slab may be used, and embodiments are not limited to use of maximum intensity projection.

Turning again to the process of FIG. 2, at stage 122 the image generation circuitry 28 generates the two-dimensional output image for display on display screen 16 using the pixel values determined at stage 120. Each pixel of the two-dimensional image corresponds to a respective ray path 500. Since the ray paths 500 are defined in a tilted cylindrical configuration, the two-dimensional image provides an unfolded view of the ribs in which at least some of the ribs may appear to be substantially horizontal.

In the present embodiment, the user can control the presentation of the output image using pan and zoom tools to allow the user to focus in on an area of interest. The image generation circuitry 28 may update the two-dimensional output image in response to user input. Additional triangulation tools may be used which allow navigation between an unfolded view and axial MPR views of the same data. For example, the user may click on the axial MPR views and the corresponding point on the unfolded view may be highlighted, and vice versa.

The two-dimensional image may be described as an advanced curved MPR view (or CPR view, curved planar reformatting view) that intersects all of the patient's ribs. The advanced curved MPR view may allow all of the ribs to be visualised at once. By visualising all the ribs at once, it may be easier for a clinician to identify on which rib a fracture or lesion has occurred. It may be faster for the clinician to view all ribs at once using the curved MPR view, rather than to step through a set of axial or oblique MPR views.

The two-dimensional image is obtained using a two-step process. The first step of the two-step process comprises determining the manifold which intersects all the structures of interest. The second step of the two-step process comprises mapping points in the 2D target image to points of the manifold surface and sampling those points of the manifold surface to use for colour lookup to determine the final pixel colours.

Using a two-step process including determining a manifold may allow particular anatomy, such as the ribs, to be imaged in a way that is useful to the user. For example, in the present embodiment, the two-step process may allow effective visualisation of fractures of the ribs. In other embodiments, the two-step process may allow effective visualisation of other anatomical structures.

The determination of the manifold that passes through the ribs may allow a visualisation of a surface that passes though the ribs to be obtained, for example a visualisation of a surface that passes through the middle of the ribs. The view produced may be different to a view produced by other methods, for example by a method that uses maximum intensity projection without determining a manifold. Showing an image based on intensities for points on a manifold 400 passing through the ribs, rather than an image based on maximum intensities, may provide an improved view of fractures.

The method of FIG. 2 may provide improved visibility of non-displaced fractures. The thin CPR view may make non-displaced fractures visible. The method may be particularly useful if there are fractures near the spine. Fractures near the spine may be more visible than may be the case if using some previously-known methods. The method of FIG. 2 may provide an improved view of bone lesions.

An unfolded projection is used in the process of FIG. 2. A complex manifold 400 that intersects all of the patient's ribs is automatically extracted. The manifold 400 that is used to create the image may be substantially continuous. A projection system is used to display a 2D image where pixels correspond to the points on the manifold surface.

The method of FIG. 2 comprises obtaining a manifold 400 that intersects the ribs. The manifold is based on the mid-points of the ribs, so may pass through or near the middle of the ribs. In other embodiments, the manifold determination circuitry 24 is configured to obtain a modified manifold by varying a boundary of the manifold. Varying the boundary of the manifold may comprise enlarging or shrinking the manifold. An offset may be applied to the manifold 400 to expand or contract it.

For example, in some embodiments, the manifold determination circuitry 24 offsets points on the manifold outwards with respect to the axis to obtain an expanded manifold. The image generation circuitry 28 performs a ray casting process as described above with reference to FIG. 2, using the expanded manifold. The image generation circuitry 28 thereby obtains a further image based on the expanded manifold. The expanded manifold may pass through an outer part of each ribs, for example at or near an outer surface of each rib, rather than through the centre of each rib.

In some embodiments, the manifold determination circuitry 24 offsets points on the manifold inwards, towards the axis, to obtain a contracted manifold. The contracted manifold may pass through an inner part of each rib, for example at or near an inner surface of each rib. The image generation circuitry 28 obtains an image based on the contracted manifold.

In some embodiments, the manifold determination circuitry 24 receives a user input comprising an offset value that has been selected by a user. The manifold determination circuitry 24 determines a modified manifold (which may be an expanded or contracted manifold) using the selected offset and the image determination circuitry 28 generates an image for the modified manifold.

The modified manifold may be a thin manifold (each ray may intersect the manifold at a single point) or may be a slab as described above.

Forming images based on an expanded or contracted manifold may allow an image to be formed of a surface of the ribs. Imaging the surface of the ribs may help a user to identify a fracture that does not extend all the way through the rib. Partial fractures may be identified.

Allowing a user to select the offset used to create the modified manifold may allow the user to select an offset that may provide the best view of a feature of interest, for example a fracture. If the user cannot see the fracture well in the original image, the user may vary the manifold in order to create further images.

In some embodiments, the manifold determination circuitry 24 automatically determines a plurality of modified manifolds, each having a different offset. The image determination circuitry 28 automatically determines a series of images, each using a different modified manifold. For example, the series of images may cover the entire thickness of the ribs. By stepping through the series of images, the user may view the full extent of the ribs, from outer surface to inner surface. Automatically providing such a series of images may improve the ease of use for the user. The ability to step through images through the full thickness of the ribs may provide improved detection of partial fractures, for example surface fractures.

In the embodiment described above with reference to FIG. 2, the medical imaging data set is used to determine the manifold 400. In some embodiments, the manifold determination circuitry 24 filters and/or resamples the medical imaging data set to obtain a filtered and/or resampled data set, and uses the filtered and/or resampled data set in determining the manifold 400. The filtering of the medical imaging data set may comprise using a noise-reduction filter and/or a speckle reduction filter. Using the filtered and/or resampled data set may make the algorithm used for finding the ribs more robust.

In the present embodiment, the ribs are found using an intensity threshold. Filtering may reduce the number of high-value noise voxels, so that if the filtered data set is used rather than the original medical imaging data set is used to find the rib CPR surface (i.e., the manifold 400), the rays may hit fewer high-value noise voxels.

High-value noise voxels may in some circumstances confuse the analysis phase. For example, high-value noise voxels may have an intensity that makes them appear to be voxels of bone. It may be more difficult to correctly identify voxels that are representative of rib, and therefore to find the midpoint of the intersection with the rib, if high-value noise voxels are present.

In some embodiments, the determination of the manifold 400 is performed using a filtered and/or resampled data set and the sampling of the intersection points 510 of the rays 500 and the manifold 400 is performed using the original, unfiltered, medical imaging data set. Using the filtered and/or resampled data set for the determination of the manifold 400 and the unfiltered data set for the sampling of the points may in some circumstances produce a better image than would be produced if the filtered and/or resampled data set were used for all stages, or if the unfiltered data set were used for all stages.

For example, using a filtered data set for the determination of the manifold 400 may produce a better manifold 400 by removing high-value noise pixels from the calculation. However, in the stage at which the intersection with the manifold is determined, the presence of high-value noise pixels may be less important because positions for sampling have already been defined in the manifold. It may be more important to have accurate intensity values, for example the original intensity values from the unfiltered data set.

In some embodiments, bone and/or spine segmentation may be used to constrain the search for the complex manifold and the patient's ribs. In some embodiments, bone segmentation is used to exclude non-bone areas from analysis. For example, the manifold determination circuitry 24 may use only the parts of the medical image data set that are representative of bone when estimating the manifold positions.

In some embodiments, spine segmentation is used to exclude the spine from rib finding. The use of spine segmentation may be particularly relevant when attempting to visualise fractures that are on the part of a rib that is near to the spine. Removing voxels that are representative of the spine may make it easier to estimate the manifold position, for example to find the midpoint of the rib. Removing voxels that are representative of spine may reduce the possibility of the algorithm incorrectly identifying spine as rib, and therefore incorrectly placing the manifold.

In some circumstances, if spine segmentation is not used, the manifold may be difficult to determine near the spine. It is possible that the first point identified as bone at stage 108 may be rib and the last point identified as bone may be spine, or vice versa. If one of the first point and last point is bone and the other is spine, the manifold may end up passing through soft tissue between the rib and the spine rather than correctly passing through the ribs. If the spine is instead removed by segmentation, the manifold may follow one rib then jump to the other rib, which may provide an improved representation of the ribs.

In some embodiments, a segmented version of the data set is used to obtain the manifold 400, and the original unsegmented medical imaging data set is used for the sampling of the points 510 at which the rays 500 intersect the manifold 400.

The use of filtering, bone segmentation and/or spine segmentation may make the method of finding the ribs more robust, and therefore may make the method of constructing the manifold more robust.

Figure 7:
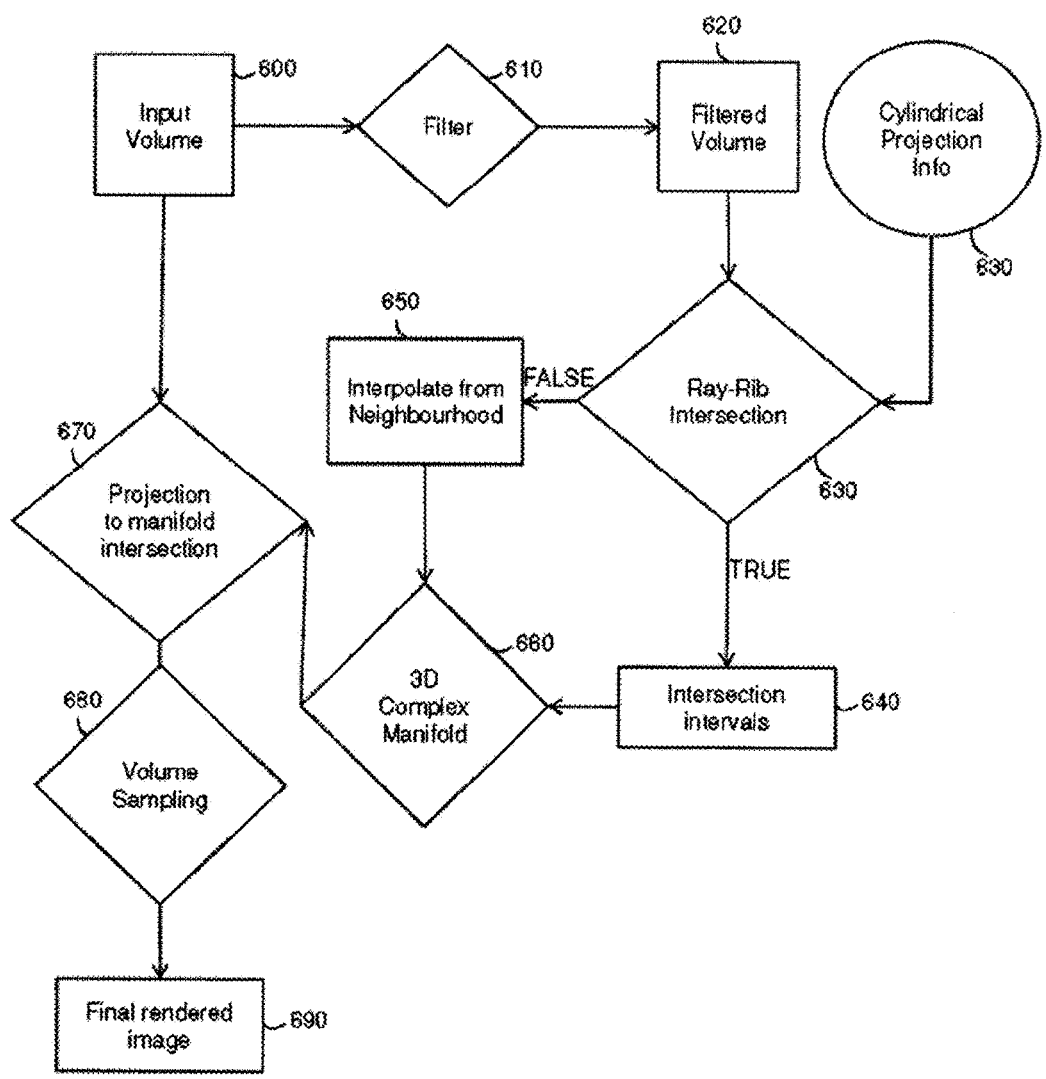
FIG. 7 is a flow chart illustrating in overview a mode of operation of the system of FIG. 1.

A further mode of operation of the system of FIG. 1 is illustrated in overview in the flow chart of FIG. 7. In the process of FIG. 7, filtered data is used to determine the manifold.

The manifold determination circuitry 24 receives an input volume 600. Input volume 600 is a medical imaging data set. At stage 610, the manifold determination circuitry 24 filters the input volume 600 to obtain a filtered volume 620. The filtered volume 620 has reduced noise when compared to input volume 600. The filtered volume 620 may also be segmented to identify bone and/or to distinguish ribs from spine.

At stage 630, the manifold determination circuitry 24 uses the filtered volume 620 and a set of cylindrical projection information 630 to determine ray-rib intersections. The cylindrical projection information 630 comprises a set of data sampling paths, for example, data sampling paths 220 on a set of tilted planes 210 as described above with reference to FIGS. 3 and 4. The ray-rib intersections comprise a set of points at which rays cast along the data sampling paths 220 intersect the ribs in the filtered volume 620.

For each data sampling path 220 that intersects a rib, the flow chart proceeds to stage 640. At stage 640, the manifold determination circuitry 24 determines an intersection interval over which the data sampling path 220 intersects the rib. The manifold determination circuitry 24 may determine a midpoint of the intersection interval.

For each data sampling path that does not intersect a rib, the flow chart proceeds to stage 650. At stage 650, the manifold determination circuitry 24 interpolates a position from the neighbourhood of the non-intersecting data sampling path. The manifold determination circuitry 24 may interpolate the position using intersection information from nearby data sampling paths, for example midpoints from nearby data sampling paths.

At stage 660, the manifold determination circuitry 24 uses the output of stages 640 and 650 to determine a three-dimensional complex manifold. For example, the manifold determination circuitry 24 may use midpoints determined at stage 640 and positions determined at stage 650 to determine the three-dimensional complex manifold.

At stage 670, the image generation circuitry 28 receives the manifold that is determined at stage 660 and the original input volume 600. The image generation circuitry 28 performs an intersection of the projection and the manifold by casting rays in dependence on the projection information 630, thereby determining a set of points on the manifold. This is the image generation projection that takes the manifold and generates the 2D rendered image. At stage 680, the image generation circuitry 28 samples the image volume 600 at the set of points that have been determined at stage 670.

At stage 690, the image generation circuitry 28 obtains pixel values corresponding to the sampled points, for example by using a transfer function, and displays a final rendered image using the pixel values. The view of the final rendered image can be slabbed or offset as necessary. For example, on viewing the rendered image, the user may select a slab thickness and/or offset and the image generation circuitry 28 may render a further image using the thickness and/or offset.

The embodiments of FIGS. 2 and 7 comprise a first ray casting to determine a complex manifold and a second ray casting to determine a rendered image. In general, any suitable method may be used for obtaining projection information (for example, a set of rays) and for obtaining a curved plane representative of at least one anatomical structure. Any suitable method of obtaining an intersection between the projection information and the curved plane may be used. Volumetric medical imaging data is then sampled at the points of intersection to obtain a final rendered image.

Embodiments have been described with reference to the imaging of ribs. However, the methods described above may be used for any appropriate anatomical structure or structures of interest that, for example, comprise a plurality of separated sub-structures. The method may be used to image any bone or bones for which an unfolded view may be useful, for example, the skull or the pelvis. Different projections may be used for different anatomical structures. The projection used for the ribs, as described above with reference to FIGS. 3 and 4, may be described as tilted cylindrical. In the case of the skull, a spherical projection may be used.

In some embodiments, the method of FIG. 2 is used for dental imaging, or for imaging of the sinuses. The method may be used to image at least one tooth or a set of teeth. In some embodiments, the method of FIG. 2 is used to image soft tissue. For example, the method may be used to image organs such as the heart, liver or stomach. The method may be used to image the coronary arteries of the heart.

A determined manifold may at least partially intersect at least one anatomical structure of interest. The manifold may at least partially fall within the interior of at least one anatomical structure of interest. The manifold may at least partially enclose a region defined by at least one anatomical structure of interest.

The method may be used with any appropriate volumetric imaging data, i.e. any volumetric imaging data in which the structures of interest are visible. Although embodiments above are described for CT imaging, the method may be used in other modalities, for example using MR imaging data sets or PET data sets.

The method may be used for obtaining an image of any appropriate subject, for example, any human or animal subject. The subject may be a patient. For example, the subject may be undergoing medical treatment.

Certain embodiments provide a medical imaging system comprising a volumetric scanner capable of acquiring a scan of a patient; an image processing system capable of deriving a complex 3D manifold structure that intersects structures of interest within the volume; a projection system that maps pixels in the output image to rays in the volume space; and a ray processing system capable of finding the intersection of a ray and the complex 3D manifold which then samples the volume at the corresponding intersection point. The sampled data value is then used to determine the final pixel colour for that ray.

The complex 3D manifold may be set up to intersect all of the patient's ribs. For each ray, a collection of sample points, each offset in the ray direction, may be used to generate a slabbed image. An IP projection method may be used to determine an output result. Bone and spine segmentation information may be used to constrain the search for the complex manifold rays and the patient's ribs. Volumetric filtering or resampling may be used to simplify the search for the intersection of the rays and the patient's ribs.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image data processing system, comprising:
processing circuitry configured to:
receive a three-dimensional medical imaging data set; and
process the received three-dimensional medical imaging data set, including
determining an axis;
determining a plurality of planes extending around the axis and tilted relative to the axis such that the planes are aligned with sub-structures, the sub-structures being comprised of at least one anatomical structure;
for each plane of the plurality of planes, casting a respective plurality of rays extending radially across the plane from the axis, and for each ray of the respective plurality of rays, estimating a respective manifold position by determining an intersection of the ray with bone;
determining a manifold that intersects bones included in the sub-structures and represents a shape of the at least one anatomical structure by using the estimated manifold positions; and
obtaining an unfolded view by sampling a plurality of points on the determined manifold.

2. The system according to claim 1, wherein the obtaining of the unfolded view by the processing circuitry comprises performing a ray casting process, the plurality of points comprising points of intersection between rays of the ray casting process and the manifold.

3. The system according to claim 2, wherein the obtaining of the unfolded view by the processing circuitry comprises determining the rays of the ray casting process by using a projection to map pixels of the unfolded view to rays of the ray casting process.

4. The system according to claim 2, wherein the performing of the ray casting process by the processing circuitry comprises, for each of at least some of the rays of the ray casting process, determining at least one value of the medical imaging data set at an intersection between said ray and the manifold, and determining a pixel value for a respective pixel of the unfolded view from said at least one value of the medical imaging data set.

5. The system according to claim 1, wherein at least one of:
the determining of the manifold comprises determining a manifold that at least partially intersects the at least one anatomical structure;
the determining of the manifold comprises determining a manifold that at least partially falls within an interior of said at least one anatomical structure; and
the manifold at least partly encloses a region defined by the at least one anatomical structure.

6. The system according to claim 1, wherein the determining of the manifold by the processing circuitry is based on an expected profile of values of the medical imaging data set across a thickness of said at least one anatomical structure.

7. The system according to claim 1, wherein the determining of the manifold by the processing circuitry comprises determining a variation of values of the medical imaging data set along a plurality of data sampling paths.

8. The system according to claim 1, wherein the determining of the manifold by the processing circuitry comprises determining part of the manifold based on values of the medical imaging data set and determining further parts of the manifold using an interpolation or extrapolation process.

9. The system according to claim 1, wherein the processing circuitry is further configured to vary a boundary or position of the manifold to obtain a modified manifold, and to determine a further image based on the modified manifold.

10. The system according to claim 9, further comprising a user input device, wherein the processing circuitry is further configured to receive a user input from the user input device and to perform the varying of the boundary or the position of the manifold in response to the user input.

11. The system according to claim 9, wherein the varying of the boundary by the processing circuitry comprises enlarging or shrinking the manifold.

12. The system according to claim 1, wherein the manifold comprises or forms part of a slab.

13. The system according to claim 11, wherein the sampling process performed by the processing circuitry comprises performing a projection across the thickness of the slab to obtain the unfolded view.

14. The system according to claim 1, wherein the processing circuitry is further configured to perform a segmentation process on the medical imaging data set to obtain a segmented data set, and at least one of the determination of the manifold and the obtaining of the unfolded view is performed using the segmented data set.

15. The system according to claim 1, wherein the processing circuitry is further configured to perform a filtering process on the medical imaging data set to obtain a filtered data set, the filtering process comprising removing or amending at least some of the data of the medical imaging data set, and wherein at least one of the determination of the manifold and the obtaining of the unfolded view is performed using the filtered data set.

16. The system according to claim 1, wherein at least one of
the plurality of substructures comprises a plurality of separated sub-structures; and
the least one anatomical structure comprises at least one rib, at least part of a ribcage, at least one of a skull, at least one tooth, at least one jaw, an organ, or a pelvis.

17. A medical image data processing method, comprising:
receiving a three-dimensional medical imaging data set;
processing the received three-dimensional medical imaging data set, including determining an axis;

determining a plurality of planes extending around the axis and tilted relative to the axis such that the planes are aligned with sub-structures, the sub-structures being comprised of at least one anatomical structure;

for each plane of the plurality of planes, casting a respective plurality of rays extending radially across the plane from the axis, and for each ray of the respective plurality of rays, estimating a respective manifold position by determining an intersection of the ray with bone;

determining a manifold that intersects bones included in the sub-structures and represents a shape of the at least one anatomical structure by using the estimated manifold positions; and obtaining an unfolded view by sampling a plurality of points on the determined manifold.

* * * * *